(12) United States Patent
Ishii et al.

(10) Patent No.: US 11,324,402 B2
(45) Date of Patent: May 10, 2022

(54) LASER DEVICE AND PHOTOACOUSTIC MEASUREMENT APPARATUS

(71) Applicant: FUJIFILM Corporation, Tokyo (JP)

(72) Inventors: Hiroyasu Ishii, Kanagawa (JP); Kazuhiro Hirota, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 663 days.

(21) Appl. No.: 16/142,384

(22) Filed: Sep. 26, 2018

(65) Prior Publication Data

US 2019/0021604 A1    Jan. 24, 2019

Related U.S. Application Data

(63) Continuation of application No. PCT/JP2017/006701, filed on Feb. 23, 2017.

(30) Foreign Application Priority Data

Mar. 30, 2016 (JP) .............................. JP2016-067328

(51) Int. Cl.
*A61B 5/00* (2006.01)
*H01S 3/115* (2006.01)
(Continued)

(52) U.S. Cl.
CPC ........ *A61B 5/0095* (2013.01); *H01S 3/10046* (2013.01); *H01S 3/115* (2013.01);
(Continued)

(58) Field of Classification Search
CPC ...... H01S 3/115; H01S 3/1109; G02F 1/0131; G02F 1/03–076
See application file for complete search history.

(56) References Cited

U.S. PATENT DOCUMENTS 1,694,661 A * 12/1928 Meissner .............. G02F 1/0131
358/302
3,694,769 A * 9/1972 Hook ...................... H01S 3/115
372/12
(Continued)

FOREIGN PATENT DOCUMENTS

CN          1983746 A      6/2007
CN       105231992 A  *  1/2016   ........... H01S 3/1305
(Continued)

OTHER PUBLICATIONS

Chinese Office Action dated Nov. 5, 2019 for Chinese Patent Application No. 201780020725.9 with partial English translation.
(Continued)

*Primary Examiner* — Joshua King
(74) *Attorney, Agent, or Firm* — Birch, Stewart, Kolasch & Birch, LLP

(57) ABSTRACT

A Q switch is vibrated by applying a first voltage, and pulsed laser light is emitted by applying a second voltage to the Q switch at a point in time at which a preset delay time has passed from the start of emission of excitation light. Then, in this case, a time which is within a period, for which the vibration of the Q switch continues, and at which the intensity of the pulsed laser light periodically changing due to the vibration of the Q switch is maximized in a case where a point in time of application of the second voltage to the Q switch is changed is set as the delay time.

11 Claims, 6 Drawing Sheets

(51) Int. Cl.
  *H01S 3/10* (2006.01)
  *H01S 3/136* (2006.01)
  *A61B 8/00* (2006.01)
  *H01S 3/06* (2006.01)
  *H01S 3/08* (2006.01)
  *H01S 3/092* (2006.01)

(52) U.S. Cl.
  CPC .............. *H01S 3/136* (2013.01); *A61B 5/002* (2013.01); *A61B 5/7225* (2013.01); *A61B 8/4416* (2013.01); *A61B 2562/0247* (2013.01); *H01S 3/061* (2013.01); *H01S 3/08054* (2013.01); *H01S 3/092* (2013.01); *H01S 3/10069* (2013.01)

(56) References Cited

U.S. PATENT DOCUMENTS

| | | | | |
|---|---|---|---|---|
| 3,783,406 | A * | 1/1974 | Hook | H01S 3/115 372/12 |
| 3,830,557 | A * | 8/1974 | Hook | H01S 3/115 359/255 |
| 3,836,866 | A * | 9/1974 | Ammann | H01S 3/115 372/12 |
| 4,197,513 | A * | 4/1980 | Bell | H01S 3/115 372/12 |
| 4,375,684 | A * | 3/1983 | Everett | H01S 3/115 372/12 |
| 4,528,668 | A * | 7/1985 | Wayne | H01S 3/107 372/108 |
| 4,959,838 | A * | 9/1990 | Barnes | H01S 3/115 372/25 |
| 5,394,415 | A * | 2/1995 | Zucker | G02F 1/0126 372/10 |
| 5,982,790 | A * | 11/1999 | Grossman | H01S 3/13 372/10 |
| 2008/0018977 | A1* | 1/2008 | Bergmann | G02F 1/0327 359/257 |
| 2014/0376574 | A1* | 12/2014 | Skrabelj | G02F 1/0327 372/12 |
| 2015/0207292 | A1* | 7/2015 | Jonuska | H01S 3/091 372/12 |
| 2016/0226214 | A1* | 8/2016 | Ishii | H01S 3/115 |
| 2019/0280455 | A1* | 9/2019 | Haefner | G02F 1/0136 |

FOREIGN PATENT DOCUMENTS

| | | | | |
|---|---|---|---|---|
| CN | 106253043 | A * | 12/2016 | |
| CN | 108110604 | A * | 6/2018 | |
| CN | 105720476 | B * | 11/2018 | |
| DE | 102015106728 | A1 * | 8/2016 | ........... H01S 3/1024 |
| DE | 102016122705 | B3 * | 3/2018 | ............. H01S 3/107 |
| EP | 0105887 | A4 * | 7/1986 | ........... H01S 3/1075 |
| EP | 1180834 | A2 * | 2/2002 | ......... B23K 26/0643 |
| GB | 1166922 | A | 10/1969 | |
| JP | 45-8272 | B | 3/1970 | |
| JP | 59-104558 | U | 7/1984 | |
| JP | 1-70372 | U | 5/1989 | |
| JP | 5-299752 | A | 11/1993 | |
| JP | 9-181375 | A | 7/1997 | |
| JP | 10-247755 | A | 9/1998 | |
| JP | 2005-268415 | A | 9/2005 | |
| JP | 2015012012 | A * | 1/2015 | ........... H01S 3/1317 |
| JP | 2015-111660 | A | 6/2015 | |
| JP | 2015-525003 | A | 8/2015 | |
| WO | WO-2013146197 | A1 * | 10/2013 | ........... B23K 26/354 |
| WO | WO-2015001876 | A1 * | 1/2015 | ......... G01N 29/2418 |
| WO | WO-2017171595 | A1 * | 10/2017 | ........... H01S 3/1305 |

OTHER PUBLICATIONS

Japanese Notice of Reasons for Refusal dated Jun. 4, 2019, for Japanese Patent Application No. 2018-508594, with English translation.
International Preliminary Report on Patentability and Written Opinion of the International Searching Authority (Forms PCT/IB/326, PCT/IB/373 and PCT/ISA/237) for International Application No. PCT/JP2017/006701, dated Oct. 11, 2018, with English translation.
International Search Report (Form PCT/ISA/210) for International Application No. PCT/JP2017/006701, dated May 9, 2017, with English translation.

* cited by examiner

--PRIOR ART--

LASER DEVICE AND PHOTOACOUSTIC MEASUREMENT APPARATUS

CROSS-REFERENCE TO RELATED APPLICATIONS

This application is a continuation application of International Application No. PCT/JP2017/006701, filed Feb. 23, 2017, the disclosure of which is incorporated herein by reference in its entirety. Further, this application claims priority from Japanese Patent Application No. 2016-067328, filed Mar. 30, 2016, the disclosure of which is incorporated herein by reference in its entirety.

BACKGROUND

1. Technical Field

The present invention relates to a laser device and more particularly, to a laser device that emits pulsed laser light as a giant pulse by resonating laser light emitted from a laser medium with a resonator. In addition, the present invention relates to a photoacoustic measurement apparatus including such a laser device.

2. Related Art

As a kind of image examination method capable of examining the state of the inside of the living body in a non-invasive manner, an ultrasound examination method is known. In ultrasound examination, an ultrasound probe capable of transmitting and receiving ultrasound waves is used. In a case where ultrasound waves are transmitted to a subject (living body) from the ultrasound probe, the ultrasound waves propagate through the living body and are reflected on the tissue interface. By receiving the reflected ultrasound waves using the ultrasound probe and calculating the distance based on the time until the reflected ultrasound waves return to the ultrasound probe, it is possible to image the state of the inside.

In addition, photoacoustic imaging for imaging the inside of the living body using the photoacoustic effect is known. In general, in the photoacoustic imaging, pulsed laser light, such as a laser pulse, is emitted into the living body. In the living body, the living tissue absorbs the energy of the pulsed laser light, and ultrasound waves (photoacoustic signal) are generated by adiabatic expansion due to the energy. By detecting the photoacoustic signal using an ultrasound probe or the like and forming a photoacoustic image based on the detected signal, it is possible to visualize the inside of the living body based on the photoacoustic signal.

For measurement of photoacoustic waves, it is necessary to emit pulsed laser light with high intensity in many cases. As a light source, a solid state laser device that emits pulsed laser light as a giant pulse by performing Q switch pulse oscillation is used in many cases. The laser device has a laser rod and a flash lamp for exciting the laser rod. The laser device has a Q switch for Q switch pulse oscillation. A laser device that can be used for photoacoustic measurement is disclosed in, for example, JP2005-268415A or JP1993-299752A (JP-H05-299752A).

SUMMARY

In a case where a voltage applied to an electro-optical element used as a Q switch changes, the crystal of the electro-optical element is deformed, and the characteristics of the crystal change with time. As a result, an adverse effect, such as a reduction in the output of pulsed laser light, occurs. JP2005-268415A discloses a method for suppressing the adverse effect.

JP1993-299752A (JP-H05-299752A) also describes vibration (expressed as sound waves in JP1993-299752A (JP-H05-299752A)) generated due to deformation of the electro-optical element. Since such a vibration results in a reduction in the output of the pulsed laser light, JP1993-299752A (JP-H05-299752A) discloses a method for suppressing the vibration of the electro-optical element.

Thus, it is known that the vibration generated in the case of changing the voltage applied to the electro-optical element used as a Q switch causes a reduction in the output of the pulsed laser light. Conventionally, countermeasures have been taken to reduce the adverse effect due to the vibration of the Q switch.

Contrary to the conventional countermeasures, it is an object of the present invention to provide a laser device having improved output of pulsed laser light by actively using the vibration of the Q switch, which has been considered to have an adverse effect in the related art, and a photoacoustic measurement apparatus including the laser device.

A laser device of the present invention comprises: an excitation light source that emits excitation light; a laser medium that receives the excitation light emitted from the excitation light source and emits laser light; a resonator that includes a pair of mirrors with the laser medium interposed therebetween and that emits pulsed laser light by resonating the laser light between the pair of mirrors; a Q switch that is disposed in an optical path of the resonator to change a Q value of the resonator according to an applied voltage and that makes a Q value of the resonator in a case where a first voltage is applied lower than a Q value of the resonator in a case where a second voltage different from the first voltage is applied; a Q switch driving unit that drives the Q switch by applying the first voltage and the second voltage to the Q switch; and a controller that controls the excitation light source and the Q switch driving unit to emit the excitation light to the laser medium in a case where a voltage applied to the Q switch is the first voltage and change the voltage applied to the Q switch from the first voltage to the second voltage after the emission of the excitation light such that the pulsed laser light is emitted from the resonator. The controller vibrates the Q switch by applying the first voltage, and applies the second voltage to the Q switch at a point in time at which a preset delay time has passed from start of emission of the excitation light. The delay time is set to a time which is within a period, for which vibration of the Q switch continues, and at which an intensity of the pulsed laser light periodically changing due to the vibration of the Q switch is maximized in a case where a point in time of application of the second voltage to the Q switch is changed.

In the laser device of the present invention, it is preferable that the controller starts application of the first voltage to the Q switch simultaneously with emission start timing of the excitation light.

In the laser device of the present invention, it is preferable that the first voltage is a voltage higher than the second voltage.

In the laser device of the present invention, it is preferable that a rise time of the first voltage is 2 µs or less.

In the laser device of the present invention, it is preferable that the rise time of the first voltage is 1 µs or less.

The laser device of the present invention may further comprise a delay time changing unit that receives a change in the delay time.

The laser device of the present invention may further comprise a storage unit in which a periodic change in the intensity of the pulsed laser light due to the vibration of the Q switch is stored in advance.

The laser device of the present invention may further comprise a display controller that displays the periodic change in the intensity of the pulsed laser light stored in the storage unit on a display unit.

The laser device of the present invention may further comprise a light detection unit that detects a periodic change in the intensity of the pulsed laser light.

A photoacoustic measurement apparatus of the present invention comprises: the laser device of the present invention described above; and a probe that detects photoacoustic waves, which are generated in a subject due to irradiation of pulsed laser light emitted from the laser device to the subject, and outputs a photoacoustic wave signal.

The photoacoustic measurement apparatus of the present invention may further comprise an acoustic image generation unit that generates a photoacoustic image based on the photoacoustic wave signal output from the probe.

In the photoacoustic measurement apparatus of the present invention, the probe may detect a reflected wave of an acoustic wave transmitted to the subject and output a reflected wave signal, and the acoustic image generation unit may generate a reflected acoustic image based on the reflected wave signal.

According to the laser device and the photoacoustic measurement apparatus of the present invention, the Q switch is vibrated by applying the first voltage, and the pulsed laser light is emitted by applying the second voltage to the Q switch at a point in time at which the preset delay time has passed from the start of the emission of the excitation light. Then, in this case, a time which is within a period, for which the vibration of the Q switch continues, and at which the intensity of the pulsed laser light periodically changing due to the vibration of the Q switch is maximized in a case where the point in time of application of the second voltage to the Q switch is changed is set as the delay time. As a result, it is possible to emit pulsed laser light with higher power than in a case where the Q switch is not vibrated.

BRIEF DESCRIPTION OF THE DRAWINGS

Exemplary embodiments according to the technique of the present disclosure will be described in detail based on the following figures, wherein.

DETAILED DESCRIPTION

Figure 1:
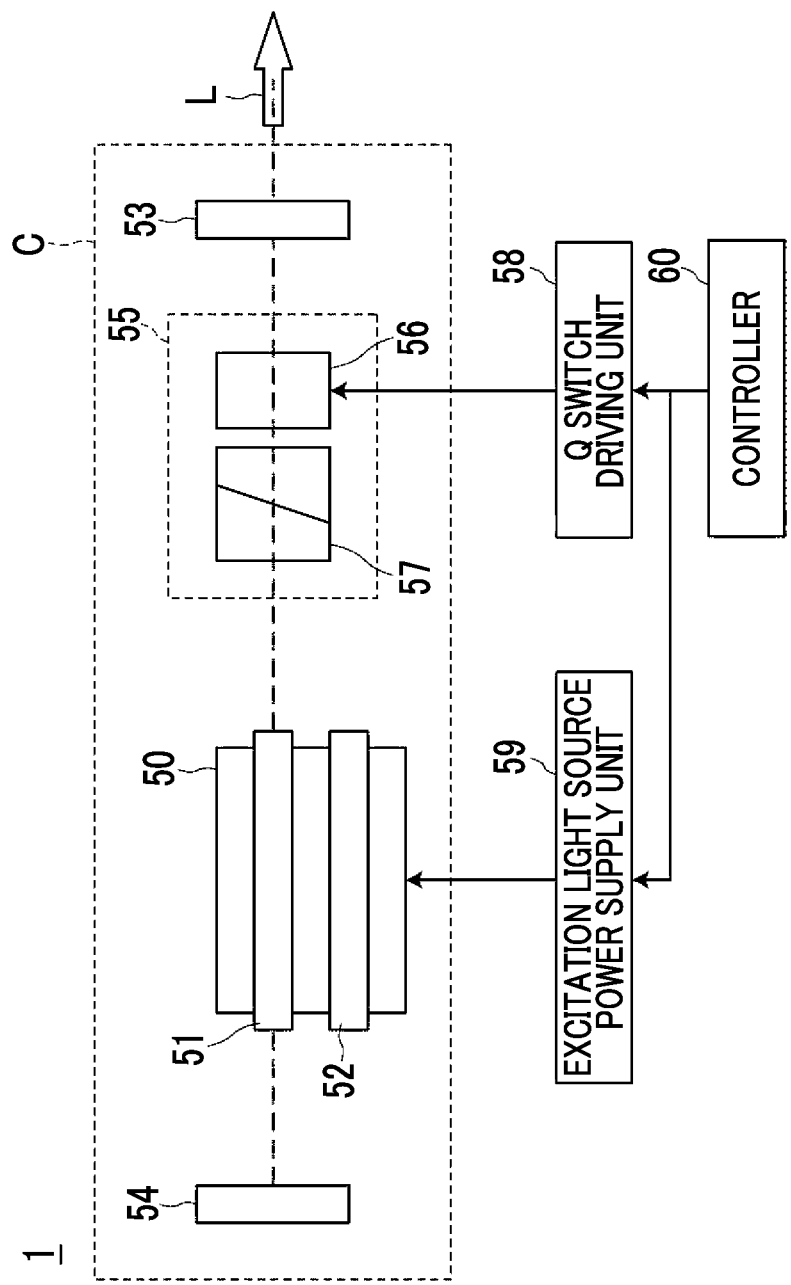
FIG. 1 is a diagram showing the schematic configuration of a first embodiment of a laser device of the present invention.

Hereinafter, a first embodiment of a laser device of the present invention will be described in detail with reference to the diagrams. FIG. 1 is a diagram showing the schematic configuration of a laser device 1 of the present embodiment.

As shown in FIG. 1, the laser device 1 of the present embodiment includes a laser rod 51, a flash lamp 52, a laser chamber 50, a first mirror 53, a second mirror 54, a Q value changing unit 55, a Q switch driving unit 58, an excitation light source power supply unit 59, and a controller 60.

The flash lamp 52 emits excitation light. The flash lamp 52 is intermittently driven by the high voltage output from the excitation light source power supply unit 59, and emits pulsed excitation light. The flash lamp 52 corresponds to an excitation light source of the present invention. The excitation light source is not limited to the flash lamp 52, and other excitation light sources may be used.

The laser rod 51 is a bar-shaped laser medium, and receives the excitation light emitted from the flash lamp 52 and emits laser light. As the laser rod 51, for example, alexandrite crystal can be used, but other known laser mediums can be used without being limited thereto.

The laser rod 51 and the flash lamp 52 are housed in the laser chamber 50. A reflection surface is provided inside the laser chamber 50, and the light emitted from the flash lamp 52 is directly emitted to the laser rod 51 or is reflected on the reflection surface and emitted to the laser rod 51. The inside of the laser chamber 50 may be a diffuse reflection surface.

The first mirror 53 and the second mirror 54 are arranged along the optical axis of the laser rod 51. The first mirror 53 and the second mirror 54 are arranged so as to face each other with the laser rod 51 interposed therebetween. The laser light emitted from the laser rod 51 is reflected by the first mirror 53 and the second mirror 54 and reciprocates between the first mirror 53 and the second mirror 54. That is, a resonator C is formed by the first mirror 53 and the second mirror 54. The first mirror 53 is an output coupler (OC). Then, by the control of the Q value of the resonator C by the Q value changing unit 55, the pulsed laser light L is emitted from the first mirror 53.

In the present embodiment, the first mirror 53 and the second mirror 54 are arranged along the optical axis of the laser rod 51 to form the optical path of the resonator C in a linear shape. However, the present invention is not limited thereto, and a prism or the like may be provided on the optical path between the first mirror 53 and the second mirror 54 to bend the optical axis.

The Q value changing unit 55 is inserted in the optical path of the resonator C to change the Q value of the resonator. In the present embodiment, the Q value changing unit 55 is disposed between the first mirror 53 and the laser rod 51. However, the Q value changing unit 55 may be disposed between the laser rod 51 and the second mirror 54 without being limited thereto. The Q value changing unit 55 includes a Q switch 56 and a polarizer 57.

The Q switch 56 changes the Q value of the resonator C by changing the polarization state of light transmitted therethrough according to the applied voltage. As the Q switch 56, it is possible to use an electro-optical element that changes the polarization state of light transmitted therethrough according to the applied voltage. For example, a Pockels cell can be used as the Q switch 56.

The Q switch 56 changes the state of the resonator C to a low Q state in a case where a first voltage corresponding to Q switch OFF is applied. The low Q state is a state in which the Q value of the resonator C is lower than a laser oscillation threshold value. The Q switch OFF refers to the state of the Q switch 56 that changes the state of the resonator C to the low Q state as described above. The Q switch 56 of the present embodiment functions as a quarter wavelength plate in a case where the first voltage is applied.

The Q switch 56 changes the state of the resonator C to a high Q state in a case where a second voltage corresponding to Q switch ON is applied. The high Q state is a state in which the Q value of the resonator C is higher than the laser oscillation threshold value. The Q switch ON refers to the state of the Q switch 56 that changes the state of the resonator C to the high Q state as described above. The Q switch 56 of the present embodiment does not change the polarization state of light transmitted therethrough in a case where the second voltage is applied.

The relationship between the first voltage and the second voltage is that the absolute value of the first voltage is larger than the absolute value of the second voltage. The second may be a positive voltage or a negative voltage. The second voltage can be set to, for example, 0 V (no voltage applied).

The polarizer 57 is disposed between the laser rod 51 and the Q switch 56. The polarizer 57 allows only linearly polarized light in a predetermined direction to pass therethrough. As the polarizer 57, for example, a beam splitter that transmits linearly polarized light in a predetermined direction and reflects linearly polarized light in a direction perpendicular to the predetermined direction can be used. In the present embodiment, a beam splitter that transmits p-polarized light and reflects s-polarized light is used as the polarizer 57. The polarizer 57 may be omitted in a case where the laser rod 51 itself has polarized light selectivity, such as a case where alexandrite crystal is used as the laser rod 51.

Specifically, in a case where the first voltage is applied to the Q switch 56, the Q switch 56 functions as a quarter wavelength plate as described above. First, p-polarized light incident on the polarizer 57 from the laser rod 51 passes through the polarizer 57, and becomes circularly polarized light at the time of passing through the Q switch 56. Then, the circularly polarized light transmitted through the Q switch 56 is reflected by the first mirror 53 and is then incident on the Q switch 56 again from the opposite direction. The circularly polarized light incident on the Q switch 56 in the opposite direction becomes linearly polarized light again at the time of passing through the Q switch 56, but is incident on the polarizer 57 as s-polarized light rotated by 90° and is emitted to the outside of the optical path of the resonator C. Accordingly, laser oscillation does not occur in the laser rod 51.

On the other hand, in a case where the voltage applied to the Q switch 56 is the second voltage (0 V), the p-polarized light incident on the polarizer 57 from the laser rod 51 passes through the Q switch 56 without changing the polarization state and is reflected by the first mirror 53. The light reflected by the first mirror 53 also passes through the Q switch 56 without changing the polarization state, further passes through the polarizer 57, and returns to the laser rod 51. In this manner, laser oscillation occurs.

As described above, in a case where the first voltage is applied to the Q switch 56, the Q switch 56 is made to function as a quarter wavelength plate, so that the laser light emitted from the laser rod 51 is emitted to the outside of the optical path of the resonator C and as a result, the resonator C can be changed to the low Q state. On the other hand, in a case where the second voltage is applied to the Q switch 56, the Q switch 56 is not made to function as a quarter wavelength plate, so that the incident laser light passes through the Q switch 56 as it is and as a result, the resonator C can be changed to the high Q state.

Figure 2:
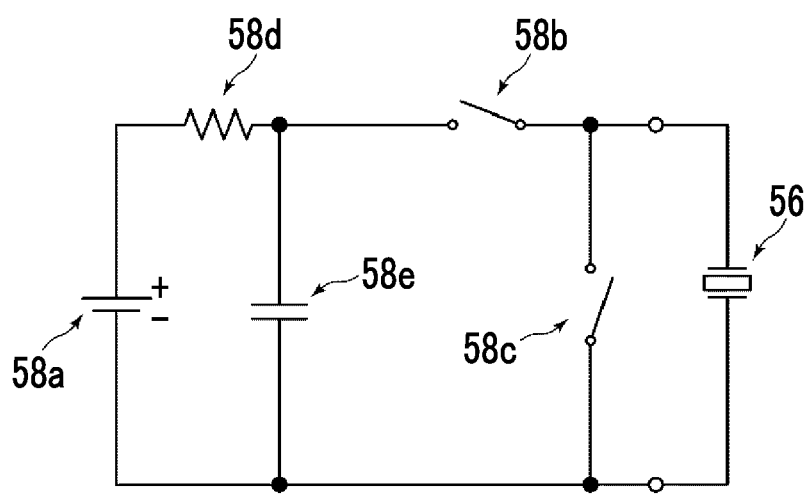
FIG. 2 is a schematic diagram showing the schematic configuration of a Q switch driving unit.

The Q switch driving unit 58 drives the Q switch 56 by applying the first voltage and the second voltage described above to the Q switch 56. FIG. 2 is a diagram schematically showing the Q switch driving unit 58, and is a diagram showing the schematic configuration of the Q switch driving unit 58. As shown in FIG. 2, the Q switch driving unit 58 includes a high voltage source 58a, a resistive element 58d and a first switch 58b that are connected in series to the high voltage source 58a, and a capacitive element 58e and a second switch 58c that are connected in parallel to the high voltage source 58a.

Figure 3:
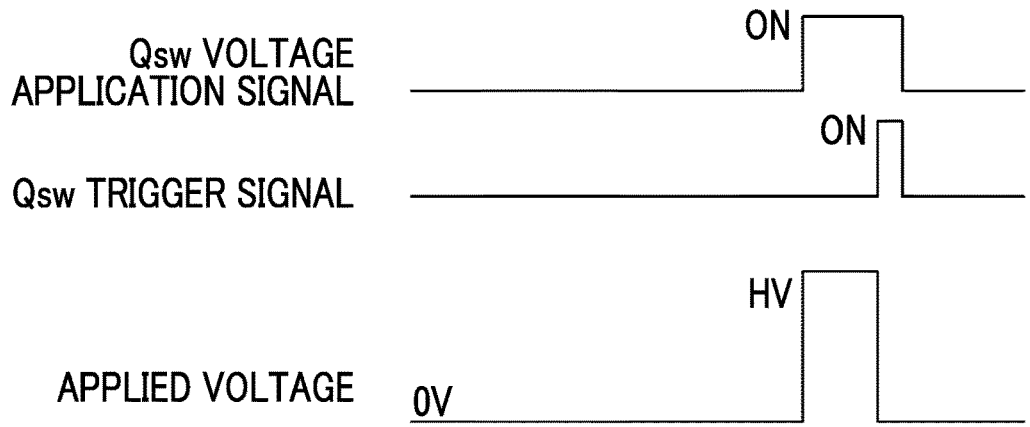
FIG. 3 is a diagram showing the relationship between a signal output from a controller and a voltage output from a Q switch driving unit.

The Q switch driving unit 58 applies a voltage to the Q switch 56 based on the signal output from the controller 60. FIG. 3 is a diagram showing the relationship between the signal output from the controller 60 and the voltage output from the Q switch driving unit 58. The controller 60 outputs a Qsw voltage application signal and a Qsw trigger signal to the Q switch driving unit 58. Then, according to the ON signal of the Qsw voltage application signal output from the controller 60, the first switch 58b of the Q switch driving unit 58 is turned on to apply a first voltage HV to the Q switch 56. At this time, the second switch 58c is in the OFF state.

In this manner, by turning on the first switch 58b connected in series to the high voltage source 58a to apply the voltage to the Q switch 56, it is possible to make the rise of the applied voltage sharp. The rise time of the applied voltage is preferably 2 μs or less, more preferably 1.5 μs or less, and even more preferably 1 μs or less. The rise time of the applied voltage is a time until the applied voltage reaches the first voltage HV from 0 V.

Then, according to the ON signal of the Qsw trigger signal output from the controller 60, the second switch 58c of the Q switch driving unit 58 is turned on. As a result, the voltage applied to the Q switch 56 becomes the second voltage (0 V). Then, the first switch 58b is turned off according to the OFF signal of the Qsw voltage application signal, and the second switch 58c is turned off according to the OFF signal of the Qsw trigger signal.

Here, in a case where a sharp rise voltage is applied to the Q switch 56 that is an electro-optical element, the Q switch 56 vibrates due to the deformation of crystal forming the Q switch 56. The laser device 1 of the present embodiment is configured to obtain the high-power pulsed laser light L by using the vibration of the Q switch 56. The method of obtaining the high-power pulsed laser light L by using the vibration of the Q switch 56 will be described in detail later.

The excitation light source power supply unit 59 applies a high voltage to the flash lamp 52 according to an FL trigger signal output from the controller 60.

The controller 60 controls the applied voltage output from the Q switch driving unit 58 by outputting the Qsw voltage application signal and the Qsw trigger signal to the Q switch driving unit 58 as described above. In addition, the controller 60 controls the high voltage output from the excitation light source power supply unit 59 by outputting the FL trigger signal to the excitation light source power supply unit 59. The controller 60 includes a central processing unit (CPU) and the like.

Figure 4:
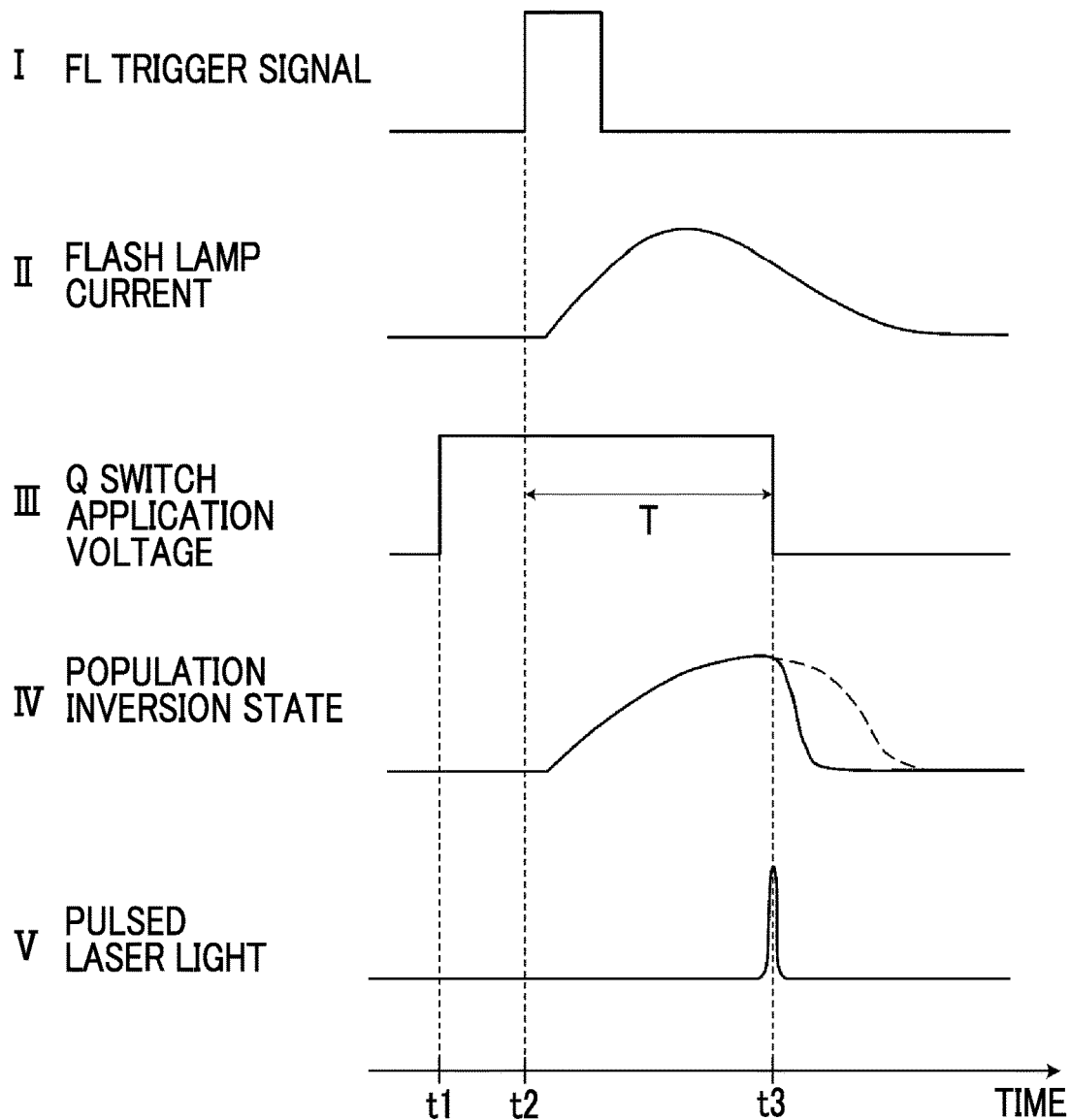
FIG. 4 is a timing chart illustrating the operation of the laser device of the first embodiment.

Next, the operation of the laser device 1 of the present embodiment will be described with reference to FIG. 4. I of FIG. 4 shows the output timing of the FL trigger signal. II of FIG. 4 shows a temporal change in a current flowing through the flash lamp 52 in a case where a high voltage is applied. III of FIG. 4 shows a temporal change in a voltage applied to the Q switch 56. IV of FIG. 4 shows a temporal change in the population inversion state of the laser rod 51. V of FIG. 4 shows the emission timing of the pulsed laser light L.

In the laser device 1 of the present embodiment, first, the first voltage HV is applied to the Q switch 56 by the Q switch driving unit 58 at time t1 before excitation light is emitted from the flash lamp 52. At this time, the first voltage HV is applied to the Q switch 56 with a sharp rise time as described above. By this voltage application, the Q switch 56 starts vibrating.

Then, after the first voltage HV is applied to the Q switch 56, at time t2, a high voltage is applied to the flash lamp 52 by the excitation light source power supply unit 59 according to the FL trigger signal output from the controller 60, and excitation light is emitted from the flash lamp 52.

The excitation light emitted from the flash lamp 52 is emitted to the laser rod 51. Accordingly, laser light is emitted from the laser rod 51. The laser light emitted from the laser rod 51 reciprocates between the first mirror 53 and the second mirror 54. At this time, the Q switch 56 functions as a quarter wavelength plate by application of the first voltage HV, the pulsed laser light L does not oscillate since the resonator C is in the low Q state, and the population inversion of the laser rod 51 increases with the passage of time.

Then, at time t3 at which a preset delay time T has passed from the time t2 that the emission start time of excitation light, the second voltage (0 V) is applied to the Q switch 56 to turn on the Q switch 56. As a result, the resonator C changes to the high Q state, and the pulsed laser light L is emitted from the first mirror 53 of the resonator C.

Figure 5:
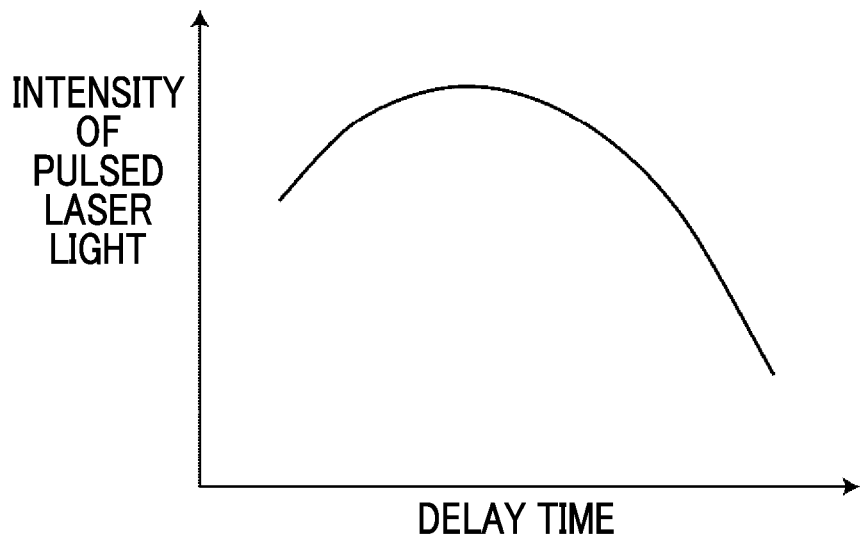
FIG. 5 is a diagram showing the relationship between the length of the delay time and the intensity of pulsed laser light in a case where a Q switch is not vibrated.

In the case of changing the delay time T described above, for example, in a case where the Q switch 56 is not vibrated as in the present embodiment, the relationship between the length of the delay time T and the intensity of the pulsed laser light L emitted from the resonator C is a relationship shown in FIG. 5. Therefore, in a case where the Q switch 56 is not vibrated, the pulsed laser light L with the highest power can be emitted by setting the delay time T to a time at which the intensity of the pulsed laser light L shown in FIG. 5 is maximized.

Figure 6:
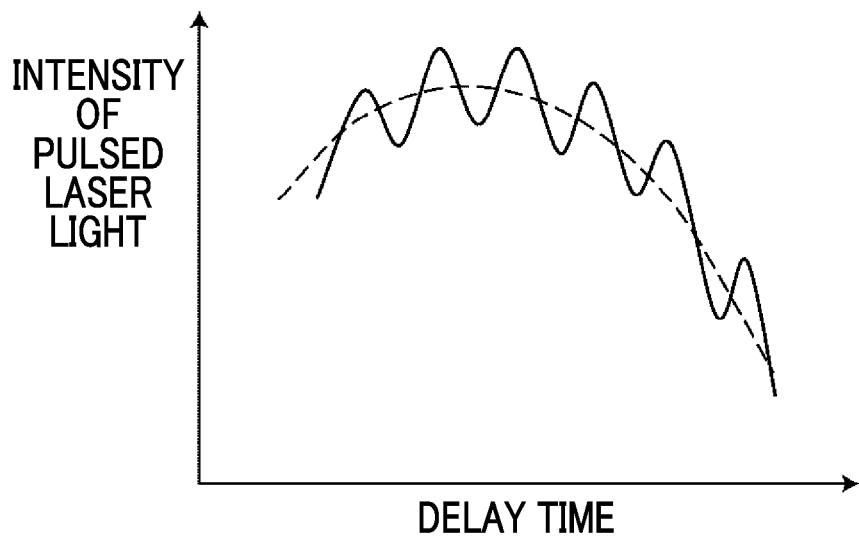
FIG. 6 is a diagram showing the relationship between the length of the delay time and the intensity of pulsed laser light L in a case where a Q switch is vibrated.

On the other hand, in the present embodiment, the Q switch 56 is vibrated by applying a voltage at a sharp rise time to the Q switch 56 as described above. Then, it was found by the inventors' research that the intensity of the pulsed laser light L periodically changed due to the vibration of the Q switch 56. FIG. 6 is a diagram showing the relationship between the length of the delay time T and the intensity of the pulsed laser light L emitted from the resonator C in a case where the Q switch 56 is vibrated. The dotted line shown in FIG. 6 indicates the intensity change of the pulsed laser light L in a case where the Q switch 56 is not vibrated. As shown in FIG. 6, by the periodic change in the intensity of the pulsed laser light L, the maximum value of the intensity of the pulsed laser light L can be made larger than that in a case where the Q switch 56 is not vibrated.

In the present embodiment, therefore, a time which is within a period, for which the vibration of the Q switch 56 continues, and at which the intensity of the pulsed laser light L periodically changing due to the vibration of the Q switch 56 is maximized is set as the delay time T. By setting the delay time T in this manner, it is possible to obtain the pulsed laser light L with higher power than the pulsed laser light L in a case where the Q switch 56 is not vibrated.

As a method of setting the delay time T in the present embodiment, for example, an operator measures the intensity of the pulsed laser light L using a photodetector or the like while changing the setting of the delay time T, and acquires the relationship between the delay time and the intensity of the pulsed laser light L shown in FIG. 6. Then, the delay time T at which the intensity of the periodically changing pulsed laser light L is maximized may be determined using the acquired relationship, and the delay time T may be determined as a final delay time T and set in the controller 60. In the case of measuring the intensity of the pulsed laser light L while changing the delay time T as described above, it is desirable that the accuracy of the time change is at least ½ or less of the period of the intensity change of the pulsed laser light L.

In the first embodiment described above, as shown in I and III of FIG. 4, at time t1 before the excitation light is emitted from the flash lamp 52, the first voltage HV is applied to the Q switch 56. However, it is preferable that the application timing of the first voltage HV to the Q switch 56 is the same as the excitation light emission start timing.

The vibration of the Q switch 56 due to the application of the first voltage HV is attenuated vibration. Accordingly, in a case where the application timing of the first voltage HV is too earlier than the excitation light emission start timing, the vibration attenuates at the time of application of the second voltage. As a result, the output of the pulsed laser light is reduced. On the other hand, in a case where the application timing of the first voltage HV is too later than the excitation light emission start timing, accumulation of population inversion due to the emission of the excitation light is prevented correspondingly.

Therefore, as described above, it is preferable that the application timing of the first voltage HV to the Q switch 56 is the same as the excitation light emission start timing. "The same as the excitation light emission start timing" referred to herein is assumed to include the range of ±20 μs from the excitation light emission start timing.

In a case where the first voltage HV is applied to the Q switch 56 at a timing before the excitation light emission start timing as in the first embodiment described above, the vibration of the Q switch 56 is attenuated before the population inversion of the laser rod 51 is sufficiently accumulated in a case where the application timing of the first voltage HV is too early. Therefore, it is preferable that the application timing of the first voltage HV is set to a timing at which the Q switch 56 vibrates with sufficient amplitude at the point in time at which the population inversion of the laser rod 51 is sufficiently accumulated.

Figure 7:
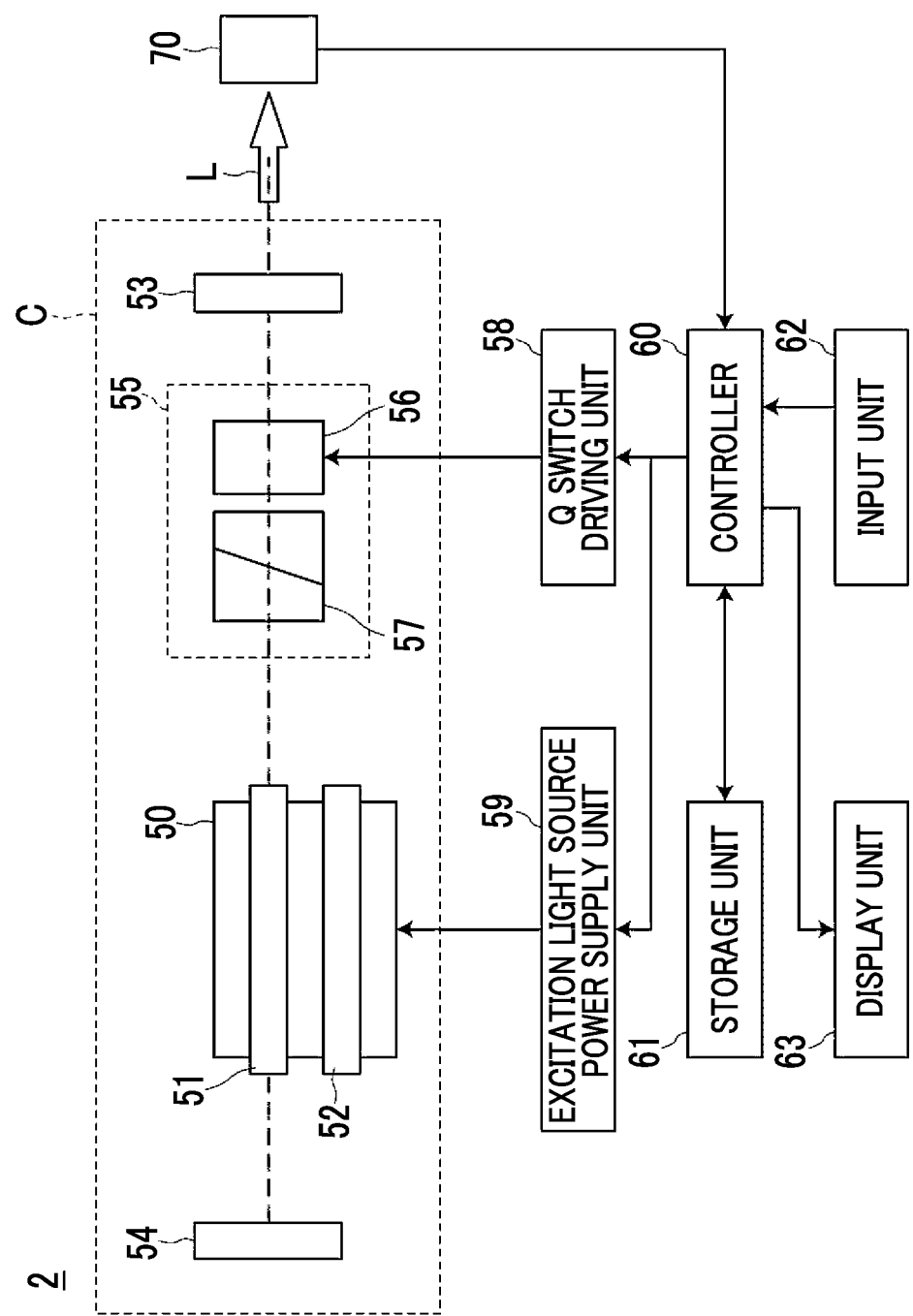
FIG. 7 is a diagram showing the schematic configuration of a laser device of a second embodiment.

Next, a second embodiment of the laser device of the present invention will be described. FIG. 7 is a diagram showing the schematic configuration of a laser device 2 of the second embodiment. The laser device 2 of the second embodiment is configured to be able to further change the delay time T set in the laser device 1 of the first embodiment. By making it possible to further change the delay time T as described above, the operator can adjust the delay time T again even in a case where the delay time T, at which the intensity of the pulsed laser light L is maximized, is shifted due to, for example, environmental influences or aging.

Specifically, the laser device 2 of the second embodiment further includes a storage unit 61, an input unit 62, a display unit 63, and a light detection unit 70. Other configurations are the same as the configurations in the laser device 1 of the first embodiment.

The input unit 62 receives a change in the delay time T by the operator. In the present embodiment, the input unit 62 corresponds to a delay time changing unit of the present invention.

The storage unit 61 is formed by a memory and the like, and a periodic change in the intensity of the pulsed laser light L caused by the vibration of the Q switch 56 described above is stored in advance in the storage unit 61. That is, the relationship (hereinafter, referred to as a periodic characteristic of the pulsed laser light L) between the delay time and the intensity of the pulsed laser light L shown in FIG. 6 is stored in advance in the storage unit 61.

In response to the instruction input through the input unit 62, the controller 60 reads out the periodic characteristic of the pulsed laser light L stored in the storage unit 61, and displays the read periodic characteristic on the display unit 63. In the present embodiment, the controller 60 corresponds to a display controller of the present invention.

The display unit 63 displays the periodic characteristic of the pulsed laser light L as described above, and is, for example, a liquid crystal touch panel also serving as the input unit 62.

The light detection unit 70 detects the intensity of the pulsed laser light L emitted from the resonator C. Specifically, the light detection unit 70 includes a light detection element, such as a photodiode.

The intensity of the pulsed laser light L detected by the light detection unit 70 is output to the controller 60. The controller 60 stores the input intensity of the pulsed laser light L and the delay time T used in acquiring the pulsed laser light L in the storage unit 61 so as to be associated with each other. The controller 60 stores the above-described periodic characteristic of the pulsed laser light L in the storage unit 61 by storing the delay time T and the intensity of the pulsed laser light L detected by the light detection unit 70 in the storage unit 61 so as to be sequentially associated with each other while changing the delay time T. In a case where the laser device 2 is actually used, the light detection unit 70 is retracted from the optical path of the pulsed laser light L.

In the laser device 2 of the second embodiment, for example, in the case of calibrating the delay time T, the operator inputs an instruction to perform the calibration using the input unit 62.

In a case where an instruction input for calibration is received through the input unit 62, the controller 60 sequentially acquires the intensity of the pulsed laser light L corresponding to the delay time T while changing the delay time T and stores the intensity of the pulsed laser light L in the storage unit 61, thereby storing the periodic characteristic of the pulsed laser light L.

Then, the controller 60 reads out the periodic characteristic of the pulsed laser light L stored in the storage unit 61, and displays the read periodic characteristic on the display unit 63. In addition, the controller 60 displays an index indicating the currently set delay time T on the display unit 63.

The operator checks the relationship between the periodic characteristic of the pulsed laser light L and the currently set delay time T, which are displayed on the display unit 63, and changes the currently set delay time T using the input unit 62. Specifically, the operator changes the setting so that the delay time T becomes the delay time of the maximum value of the periodic characteristic of the pulsed laser light L. It is desirable that the accuracy of the time change at this time is at least ½ or less of the period of the intensity change of the pulsed laser light L.

In the second embodiment described above, the periodic characteristic of the pulsed laser light L is automatically acquired. However, the present invention is not limited thereto, and the operator may measure the intensity of the pulsed laser light L while changing the delay time manually and store the relationship between the delay time and the intensity of the pulsed laser light L in the storage unit 61.

Figure 8:
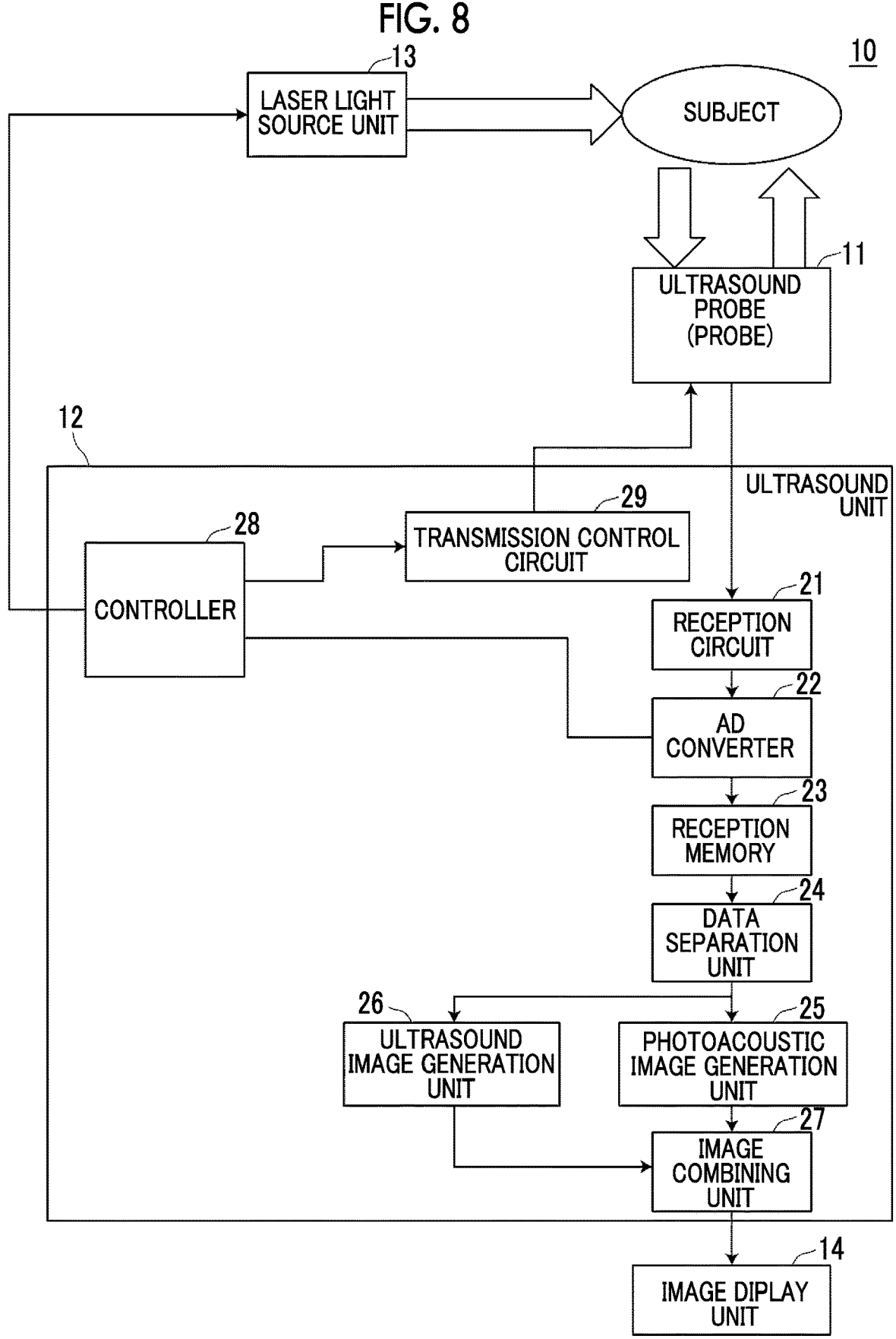
FIG. 8 is a diagram showing the schematic configuration of a photoacoustic measurement apparatus using an embodiment of the laser device of the present invention.

Next, a photoacoustic measurement apparatus using an embodiment of the laser device of the present invention will be described. FIG. 8 is a diagram showing the schematic configuration of the photoacoustic measurement apparatus.

A photoacoustic measurement apparatus 10 includes an ultrasound probe (probe) 11, an ultrasound unit 12, and a laser light source unit 13. In the present embodiment, an ultrasound wave is used as an acoustic wave. However, the present invention is not limited to the ultrasound wave, and an acoustic wave having an audible frequency may be used as long as an appropriate frequency can be selected according to an examination target, measurement conditions, or the like.

The laser light source unit 13 includes the laser device of the first or second embodiment. The pulsed laser light L emitted from the laser light source unit 13 is guided to the probe 11 by using, for example, light guiding means such as an optical fiber, and is emitted from the probe 11 to the subject. The emission position of the pulsed laser light L is not particularly limited, and the pulsed laser light L may be emitted from a place other than the probe 11.

Within the subject, ultrasound waves (acoustic waves) are generated due to a light absorber absorbing the energy of the emitted pulsed laser light L. The probe 11 has a plurality of ultrasound transducers arranged in a one-dimensional manner, for example. The probe 11 detects acoustic waves (photoacoustic waves) from the inside of the subject with a plurality of ultrasound transducers arranged in a one-dimensional manner, and outputs a photoacoustic wave signal. The probe 11 transmits acoustic waves (ultrasound waves) to the subject, detects reflected acoustic waves (reflected ultrasound waves) from the subject with respect to the transmitted ultrasound waves, and outputs a reflected wave signal. The probe 11 is not limited to the linear probe, but may be a convex probe or a sector probe.

The ultrasound unit 12 has a reception circuit 21, an analog to digital convertor (AD converter) 22, a reception memory 23, a data separation unit 24, a photoacoustic image generation unit 25, an ultrasound image generation unit 26, an image combining unit 27, a controller 28, and a transmission control circuit 29. The ultrasound unit 12 typically has a processor, a memory, a bus, and the like. Programs relevant to photoacoustic image generation and ultrasound image generation are installed on the memory of the ultrasound unit 12. By running the programs using the controller 28 configured by a processor, functions of the data separation unit 24, the photoacoustic image generation unit 25, the ultrasound image generation unit 26, and the image combining unit 27 are realized. That is, each of these units is formed by the memory on which the programs are installed and the processor.

The configuration of the hardware of the ultrasound unit 12 is not particularly limited, and can be realized by appropriately combining a plurality of integrated circuits (ICs), processors, application specific integrated circuits (ASICs), field-programmable gate arrays (FPGAs), memories, and the like.

The reception circuit 21 receives the photoacoustic wave signal output from the probe 11. In addition, the reflected wave signal output from the probe 11 is received. Typically, the reception circuit 21 includes a low noise amplifier, a variable gain amplifier, and a low pass filter. The photoacoustic wave signal and the reflected wave signal output from the probe 11 are amplified by the low noise amplifier, and then the gain is adjusted according to the depth by the variable gain amplifier and high frequency components are cut by the low pass filter.

The AD converter 22 converts the photoacoustic wave signal and the reflected wave signal received by the reception circuit 21 into digital signals. The AD converter 22 samples the photoacoustic wave signal and the reflected wave signal at predetermined sampling periods based on, for example, a sampling clock signal having a predetermined period. The AD converter 22 stores the sampled photoacoustic wave signal and reflected wave signal (sampling data) in the reception memory 23. The reception circuit 21 and the AD converter 22 may be formed as, for example, one IC, or may be formed as individual ICs.

The data separation unit 24 separates the pieces of sampling data of the photoacoustic wave signal and the reflected wave signal, which are stored in the reception memory 23, from each other. The data separation unit 24 inputs the sampling data of the photoacoustic wave signal to the photoacoustic image generation unit 25. In addition, the separated sampling data of the reflected wave signal is input to the ultrasound image generation unit 26. In the present embodiment, the photoacoustic image generation unit 25 and the ultrasound image generation unit 26 correspond to an acoustic wave image generation unit of the present invention.

The photoacoustic image generation unit 25 generates a photoacoustic image based on the photoacoustic wave signal output from the probe 11. The generation of a photoacoustic image includes, for example, image reconstruction such as phase matching addition, detection, and logarithmic conversion. The ultrasound image generation unit 26 generates an ultrasound image (reflected acoustic wave image) based on the reflected wave signal output from the probe 11. The generation of an ultrasound image also includes image reconstruction such as phase matching addition, detection, and logarithmic conversion.

The image combining unit 27 combines the photoacoustic image and the ultrasound image. The image combining unit 27 performs image combination by superimposing the photoacoustic image and the ultrasound image on each other, for example. The composite image is displayed on the image display unit 14, such as a display. Without performing image combination, the photoacoustic image and the ultrasound image may be displayed on the image display unit 14 side by side or the photoacoustic image and the ultrasound image may be switched and displayed.

The controller 28 controls each unit in the ultrasound unit 12. The controller 28 transmits a trigger signal to the laser light source unit 13, for example. In a case where the trigger signal is received, the controller 60 (FIG. 1) of the laser light source unit 13 turns on the flash lamp 52, and then switches the voltage applied to the Q switch 56 from the first voltage to the second voltage and emits the pulsed laser light L. The controller 28 controls the sampling start timing of the photoacoustic wave signal by transmitting a sampling trigger signal to the AD converter 22 in response to the emission of the pulsed laser light L.

In the case of generating an ultrasound image, the controller 28 transmits an ultrasound wave transmission trigger signal for giving an instruction of ultrasound wave transmission to the transmission control circuit 29. In a case where the ultrasound wave transmission trigger signal is received, the transmission control circuit 29 makes the probe 11 transmit ultrasound waves. The controller 28 transmits a sampling trigger signal to the AD converter 22 according to the timing of ultrasound wave transmission, thereby starting the sampling of the reflected wave signal.

In the above embodiments, a case has been described in which the probe 11 in the photoacoustic measurement apparatus 10 detects both the photoacoustic wave and the reflected ultrasound wave. However, a probe used to generate an ultrasound image and a probe used to generate a photoacoustic image do not necessarily need to be the same. The photoacoustic wave and the reflected ultrasound wave may be detected by separate probes. In the above embodiments, an example in which the laser device forms a part of the photoacoustic measurement apparatus has been described. However, the present invention is not limited thereto. The laser device of the present invention can be used for an apparatus different from the photoacoustic measurement apparatus.

What is claimed is:

1. A laser device comprising:
   an excitation light source that emits excitation light;
   a laser medium that receives the excitation light emitted from the excitation light source and emits laser light;
   a resonator that includes a pair of mirrors with the laser medium interposed therebetween and that emits pulsed laser light by resonating the laser light between the pair of mirrors;
   a Q switch that is disposed in an optical path of the resonator to change a Q value of the resonator according to an applied voltage and that makes a Q value of the resonator in a case where a first voltage is applied lower than a Q value of the resonator in a case where the first voltage is not applied;
   a Q switch driver that supplies the first voltage to the Q-switch; and
   a controller that controls the excitation light source and the Q switch driving unit to emit the excitation light to the laser medium in a case where a voltage applied to the Q switch is the first voltage and stop supplying the first voltage to the Q switch after the emission of the excitation light such that the pulsed laser light is emitted from the resonator,
   wherein the controller vibrates the Q switch by applying the first voltage, and does not apply the first voltage to the Q switch at a point in time at which a preset delay time has passed from start of emission of the excitation light, and
   the delay time is set to a time which is within a period, for which vibration of the Q switch continues, and at which an intensity of the pulsed laser light periodically changing due to the vibration of the Q switch is maximized.

2. The laser device according to claim 1,
   wherein the controller starts application of the first voltage to the Q switch simultaneously with emission start timing of the excitation light.

3. The laser device according to claim 1,
   wherein a rise time of the first voltage is 2 µs or less.

4. The laser device according to claim 3,
   wherein the rise time of the first voltage is 1 µs or less.

5. The laser device according to claim 1, further comprising:
   a delay time changing unit that receives a change in the delay time.

6. The laser device according to claim 1, further comprising:
 a storage unit in which a periodic change in the intensity of the pulsed laser light due to the vibration of the Q switch is stored in advance.

7. The laser device according to claim 6, further comprising:
 a display controller that displays the periodic change in the intensity of the pulsed laser light stored in the storage unit on a display unit.

8. The laser device according to claim 1, further comprising:
 a light detection unit that detects a periodic change in the intensity of the pulsed laser light.

9. A photoacoustic measurement apparatus comprising:
 the laser device according to claim 1; and
 a probe that detects photoacoustic waves, which are generated in a subject due to irradiation of pulsed laser light emitted from the laser device to the subject, and outputs a photoacoustic wave signal.

10. The photoacoustic measurement apparatus according to claim 9, further comprising:
 an acoustic image generation unit that generates a photoacoustic image based on the photoacoustic wave signal output from the probe.

11. The photoacoustic measurement apparatus according to claim 10,
 wherein the probe detects a reflected wave of an acoustic wave transmitted to the subject and outputs a reflected wave signal, and
 the acoustic image generation unit generates a reflected acoustic image based on the reflected wave signal.

* * * * *